US012286674B2

(12) United States Patent
Gonzales, Jr.

(10) Patent No.: US 12,286,674 B2
(45) Date of Patent: Apr. 29, 2025

(54) NUCLEIC ACID TAGGANTS

(71) Applicant: eBay Inc., San Jose, CA (US)

(72) Inventor: Sergio Pinzon Gonzales, Jr., San Jose, CA (US)

(73) Assignee: eBay Inc., San Jose, CA (US)

(*) Notice: Subject to any disclaimer, the term of this patent is extended or adjusted under 35 U.S.C. 154(b) by 431 days.

(21) Appl. No.: 17/731,006

(22) Filed: Apr. 27, 2022

(65) Prior Publication Data

US 2022/0251649 A1     Aug. 11, 2022

Related U.S. Application Data

(63) Continuation of application No. 15/972,951, filed on May 7, 2018, now Pat. No. 11,345,963.

(51) Int. Cl.
| | |
|---|---|
| *C12Q 1/6876* | (2018.01) |
| *B42D 25/36* | (2014.01) |
| *C12Q 1/6806* | (2018.01) |
| *C12Q 1/686* | (2018.01) |
| *G01N 33/68* | (2006.01) |
| *G07D 7/14* | (2006.01) |
| *G09F 3/02* | (2006.01) |
| *B42D 25/29* | (2014.01) |

(52) U.S. Cl.
CPC ........... *C12Q 1/6876* (2013.01); *B42D 25/36* (2014.10); *C12Q 1/6806* (2013.01); *C12Q 1/686* (2013.01); *G01N 33/68* (2013.01); *G07D 7/14* (2013.01); *G09F 3/02* (2013.01); *B42D 25/29* (2014.10); *G07D 2207/00* (2013.01); *G09F 2003/0282* (2013.01)

(58) Field of Classification Search
None
See application file for complete search history.

(56) References Cited

U.S. PATENT DOCUMENTS

| | | | |
|---|---|---|---|
| 6,576,422 | B1 | 6/2003 | Weinstein et al. |
| 7,667,091 | B2 | 2/2010 | Gleba et al. |
| 8,415,164 | B2 | 4/2013 | Hayward et al. |
| 9,266,370 | B2 | 2/2016 | Jung et al. |
| 9,790,538 | B2 | 10/2017 | Berrada et al. |
| 11,345,963 | B2 | 5/2022 | Gonzales |
| 2002/0064842 | A1 | 5/2002 | Sorge et al. |
| 2003/0148350 | A1 | 8/2003 | Lahnert |
| 2003/0203360 | A1 | 10/2003 | Weinstein |
| 2004/0023207 | A1 | 2/2004 | Polansky et al. |
| 2004/0137458 | A1 | 7/2004 | Archambault et al. |
| 2009/0042191 | A1 | 2/2009 | Hayward et al. |
| 2009/0197251 | A1 | 8/2009 | Melchior et al. |
| 2009/0253127 | A1 | 10/2009 | Gaudreau et al. |
| 2009/0286250 | A1 | 11/2009 | Hayward et al. |
| 2010/0190839 | A1 | 7/2010 | Kool |
| 2011/0024332 | A1 | 2/2011 | St-Onge |
| 2011/0033842 | A1 | 2/2011 | Moon et al. |
| 2011/0119778 | A1 | 5/2011 | Liss |
| 2011/0244462 | A1 | 10/2011 | Bendix et al. |
| 2013/0171630 | A1 | 7/2013 | Qin |
| 2015/0107475 | A1* | 4/2015 | Jung ........................ C12Q 1/68 101/483 |
| 2015/0320158 | A1 | 11/2015 | Duffy, Jr. et al. |
| 2016/0102215 | A1 | 4/2016 | Hayward et al. |
| 2016/0215283 | A1 | 7/2016 | Braman et al. |
| 2016/0257996 | A1 | 9/2016 | Mastaloudis et al. |
| 2016/0340297 | A1 | 11/2016 | Lemke et al. |
| 2017/0122950 | A1 | 5/2017 | Lindzen et al. |
| 2017/0292206 | A1 | 10/2017 | Jung et al. |
| 2018/0119077 | A1 | 5/2018 | Ozdoganlar et al. |
| 2018/0237854 | A1* | 8/2018 | Hogan ..................... C12Q 1/68 |
| 2019/0338354 | A1 | 11/2019 | Gonzales, Jr. |
| 2019/0382725 | A1 | 12/2019 | Prlic et al. |

FOREIGN PATENT DOCUMENTS

| | | |
|---|---|---|
| CA | 2415226 | 4/2003 |
| CN | 101233410 A | 7/2008 |
| EP | 1199371 | 4/2002 |
| EP | 1237327 | 9/2002 |
| KR | 20040076292 A | 9/2004 |
| KR | 20090057835 A | 8/2009 |
| KR | 1020140064643 | 5/2014 |
| WO | 8706383 | 10/1987 |
| WO | 2017059297 | 4/2017 |
| WO | 2019217191 | 11/2019 |

OTHER PUBLICATIONS 10-2022-7021978, "Foreign Office Action", KR Application No. 10-2022-7021978, Sep. 29, 2023, 5 pages.
201980030842.2, "Foreign Office Action", CN Application No. 201980030842.2, Nov. 4, 2023, 8 pages.
"International Preliminary Report on Patentability received for PCT Application No. PCT/US2019/030360, mailed on Nov. 19, 2020", Nov. 19, 2020, 8 Pages.
"Written Opinion received for PCT Application No. PCT/US2019/030360, mailed on Jul. 11, 2019", Jul. 11, 2019, 6 Pages.
10-2020-7028982, "Notice of Allowance received for Korean Patent Application No. 10-2020-7028982, mailed on Mar. 24, 2022", Mar. 24, 2022, 3 Pages.
10-2020-7028982, "Office Action Received for Korean Patent Application No. 10-2020-7028982, mailed on Sep. 10, 2021", Sep. 10, 2021, 4 Pages.
U.S. Appl. No. 15/972,951, "Advisory Action Received for U.S. Appl. No. 15/972,951, mailed on Dec. 14, 2020", Dec. 14, 2020, 3 Pages.
U.S. Appl. No. 15/972,951, "Applicant Initiated Interview Summary Received for U.S. Appl. No. 15/972,951, mailed on Jun. 2, 2020", Jun. 2, 2020, 4 Pages.

(Continued)

*Primary Examiner* — Samuel C Woolwine
(74) *Attorney, Agent, or Firm* — FIG. 1 Patents

(57) ABSTRACT

The present disclosure relates to compositions and methods for marking/tagging objects for identification. In particular, tagging objects with a nucleic acid taggant (genetic tag based merchandise authentication).

20 Claims, No Drawings

(56) References Cited

OTHER PUBLICATIONS

U.S. Appl. No. 15/972,951 , "Applicant Initiated Interview Summary Received for U.S. Appl. No. 15/972,951, mailed on Oct. 15, 2020", Oct. 15, 2020, 3 Pages.
U.S. Appl. No. 15/972,951 , "Final Office Action Received for U.S. Appl. No. 15/972,951, mailed on Sep. 2, 2020", Sep. 2, 2020, 9 Pages.
U.S. Appl. No. 15/972,951 , "Final Office Action received for U.S. Appl. No. 15/972,951, mailed on Jun. 25, 2021", Jun. 25, 2021, 8 Pages.
U.S. Appl. No. 15/972,951 , "Non Final Office Action Received for U.S. Appl. No. 15/972,951, mailed on Apr. 2, 2020", Apr. 2, 2020, 8 Pages.
U.S. Appl. No. 15/972,951 , "Non Final Office Action Received for U.S. Appl. No. 15/972,951, mailed on Dec. 9, 2021", Dec. 9, 2021, 6 Pages.
U.S. Appl. No. 15/972,951 , "Non Final Office Action Received for U.S. Appl. No. 15/972,951, mailed on Jan. 25, 2021", Jan. 25, 2021, 6 Pages.
U.S. Appl. No. 15/972,951 , "Notice of Allowance received for U.S. Appl. No. 15/972,951, mailed on Feb. 25, 2022", Feb. 25, 2022, 7 Pages.
U.S. Appl. No. 15/972,951 , "Response to Final Office Action filed Nov. 30, 2020, for U.S. Appl. No. 15/972,951, mailed on Sep. 2, 2020", Nov. 30, 2020, 10 pages.
U.S. Appl. No. 15/972,951 , "Response to Non-Final Office Action filed Jun. 17, 2020, for U.S. Appl. No. 15/972,951, mailed on Apr. 2, 2020", Jun. 17, 2020, 12 Pages.
BIOI4Masters , "Replication of Telomeric DNA", Retrieved from the Internet: URL: <http://mol-biol4masters.masters.grkraj.org/html/Eukaryotic_DNA_Replication5-Replication_of_Telomeric_DNA.htm>, Accessed on Jun. 7, 2018, 18 Pages.
Black , "PCR with Arbitrary Primers: Approach with Care", Insect Mol Biol 2(1), Aug. 1993, 6 Pages.
Caron , et al., "Fluorescent Labeling in Semi-solid Medium for Selection of Mammalian Cells Secreting High-levels of Recombinant Proteins", BMC Biotechnology, vol. 9, Issue No. 1, May 11, 2009, 11 Pages.
Freeman , et al., "Quantitative RT-PCR: Pitfalls and Potential", BioTechniques 26, Jan. 1999, 12 Pages.
Heid , et al., "Real Time Quantitative PCR", Genome Research 6, Oct. 1996, 9 Pages.
Jin-Hua , et al., "Reciprocal Regulation of PCGEM1 and miR-145 promote Proliferation of LNCap Prostate Cancer Cells", Journal of Experimental & Clinical Cancer Research, vol. 33, No. 1 Article No. 72, Sep. 10, 2014, 10 pages.
Min , "Telomerase Holoenzyme Proteins and Processivity Subunit in Tetrahymena Thermophila", Retrieved from the Internet: URL: <https://zupdf.com/queue/telomerase-holoenzyme-proteins-and-processivity-subunit-in-tetrahymena-thermophi_pdf?queue_id=-1&x=1528349732&z=MTE2LjUwLjU5LjE4MA==>, Jan. 1, 2009, 114 Pages.
PCT/US2019/030360 , "International Search Report received for PCT Application No. PCT/US2019/030360, mailed on Jul. 11, 2019", Jul. 11, 2019, 4 Pages.
10-2022-7021978 , "Office Action", KR Application No. 10-2022-7021978, Mar. 19, 2023, 9 pages.
19727546.4 , "Communication Pursuant to Article 94(3) EPC", EP Application No. 19727546.4, Feb. 8, 2023, 4 pages.
10-2022-7021978 , "Notice of Decision to Grant", KR Application 10-2022-7021978, May 21, 2024, 5 pages.
201980030842.2 , "Foreign Office Action", CN Application 201980030842.2, Jun. 5, 2024, 9 pages.
19727546.4 , "Foreign Office Action", EP Application No. 19727546.4, Sep. 12, 2024, 8 pages.
201980030842.2 , "Foreign Office Action", CN Application No. 201980030842.2, Sep. 24, 2024, 8 pages.

* cited by examiner

NUCLEIC ACID TAGGANTS

RELATED APPLICATION

This application is a continuation of and claims priority to U.S. patent application Ser. No. 15/972,951, filed May 7, 2018, entitled "Nucleic Acid Taggants", the entire disclosure of which is hereby incorporated by reference herein in its entirety.

BACKGROUND

Counterfeiting has become a major problem for brand names. Counterfeited goods result in a loss of trillions in revenues and millions in jobs. In addition to the revenue losses, certain counterfeit products are linked directly to health and safety issues. Counterfeit goods have infiltrated most industries from textiles to microchips, and pharmaceuticals.

Products including pharmaceuticals, toys, entertainment products, clothing, fashion accessories, money, electronics, and any other products of value have imitation counterfeits in the market for consumers. The problem with counterfeits is that they not only hurt the name of the original brand or manufacturer and the economy, but because these products are not coming from reliable sources, their quality and efficacy is likely compromised. Counterfeiting often has minimal consequences on those distributing the fake goods, compared to the consequences that could result from the malfunctioning of products with counterfeit components.

SUMMARY

The present disclosure relates to compositions and methods for marking or tagging objects for identification. In particular, the disclosure relates to tagging objects with a nucleic acid taggant (e.g. a genetic tag based merchandise authentication).

One embodiment provides a method of processing an object with a DNA taggant for authenticating or tracking comprising, a) obtaining an object that contains a DNA taggant, wherein the DNA taggant comprises telomeres; b) treating the item in a) to remove at least a portion of the DNA taggant; c) optionally purifying the removed DNA taggant of b); d) subjecting the removed DNA taggant of b) or purified DNA taggant of c) to an amplification process to produce amplified DNA taggant and analyzing the amplified DNA taggant by size and or sequence analysis; and e) subjecting the removed DNA taggant of b), purified DNA of taggant c) or the amplified DNA taggant of d) to replication, wherein said DNA taggant has telomeres and replication results in a shortening of the telomeres of said DNA taggant.

In some embodiments, the method further comprises f) coating the object with the shortened DNA taggant. In some embodiment, the method comprises repeating a)-f) two or more times on the object. In one embodiment, each time the DNA taggant is shortened in e) represents the sale of the object and the size and/or sequence of the coated DNA taggant in f) allows for the determination of the total number of times the item has been sold.

One embodiment provides a method of processing an object with a DNA taggant for authenticating or tracking comprising, a) obtaining an object that contains DNA taggant, wherein the DNA taggant comprises an expression vector which codes for a detectable protein marker; b) treating the item in a) to remove the DNA taggant; c) optionally purifying the removed DNA taggant of b); d) introducing the removed DNA taggant of b) or purified DNA taggant of c) to a host cell for transcription and translation to yield the detectable protein marker; and e) detecting the detectable protein marker from d). In some embodiments, the marker is a protein which fluoresces, provides color, provides scent, illuminates and/or is detectable with an antibody.

The methods provided herein may further comprise at least one step of searching a database for the DNA taggant, entering into a database one or more objects treated with the DNA taggant or a combination thereof.

One embodiment provides a kit comprising a DNA taggant, wherein the DNA taggant comprises telomeres or is provided in an expression vector; a DNA taggant applicator; instructions for tagging objects, one or more forms to list tagged items; a log-on ID; password or unique identifier code; one or more container; instructions for searching a web site/database; instructions for submitting information to a web site/database about objects that have been tagged; or a combination thereof.

DETAILED DESCRIPTION

Many product manufacturers utilize apparent qualities and definitive designs identifiable as "trade dress" to uniquely identify their high quality and high value products and thereby earn the trust of their customers. Others also add labels for anti-counterfeit purposes. Traditional anti-counterfeiting labels are generally formed from materials having particularly targeted physical or chemical characteristics, for example, magnetic strips on checkbooks, laser holographs on credit cards, fluorescent ink on stock certificates, and heat-sensitive inks on confidential documents. Anti-counterfeiting labels have also been made by adding specific antigens to objects that need to be identified, the antigens can then be detected with an antibody specific for the antigen. However, antigens and antibodies are proteins with characteristically poor stability under many environmental conditions of temperature and humidity, and are prone to denaturation or even degradation and consequently lose activity and can easily be destroyed, thereby reducing the accuracy and reliability of identification.

Another approach used is to add a fluorophore to the products, to be able to visually detect which products are legitimate. The fluorophore can serve as a dye or a marker for these products, which can be applied during the early stages of production throughout production or to a finished product/good. This method, although effective at first, no longer protects products as counterfeiters have copied the products along with the fluorophore. Counterfeiters were able to extract the fluorophore from the product, duplicate it, and add it to their counterfeit products, making the product fluoresce as the real product would.

Thus, nucleic acids, such as, for example, deoxyribonucleic acid (DNA) and ribonucleic acid (RNA) have been looked to as an improved alternative to commonly used anti-counterfeiting labels and markers. Despite being composed of relatively simple nucleotide building blocks, nucleic acids are capable of encoding a vast array of information: for instance, the human genome encodes all the information necessary for the synthesis and assembly of all the components of the human body from the neural networks of the brain to the intricate structures of the skeleton, tissues and organs. Nucleic acids include deoxyribonucleic acid (DNA) and the ribonucleic acid (RNA). Nucleic acid sequences can be unique and complex.

An additional advantage of nucleic acids for use as markers or taggants is that with the appropriate protection these molecules can be preserved for long periods of time. Evidence from preserved specimens in glaciers, ice sheets, tar pits and bogs and marshes shows that DNA is resilient to degradation over thousands, and in some cases millions of years. Protected taggant DNA can also be stabilized in polymers for coating of high value articles or objects of interest so as to survive long periods of time and can then be used for identification, authentication and tracking purposes. This ability to persist over long periods of time coupled with very sensitive methods to detect low numbers of molecules, for instance by amplification using the polymerase chain reaction (PCR), makes nucleic acids, and DNA in particular, an attractive candidate for use as a marker. Moreover, nucleic acids offer an almost unlimited coding capacity since the number of possible unique sequences increases fourfold with every additional base of the sequence of the oligonucleotide or polynucleotide.

Definitions

The terms "a," "an," "the" and similar referents used in the context of describing the disclosed subject matter (especially in the context of the following claims) are to be construed to cover both the singular and the plural, unless otherwise indicated herein or clearly contradicted by context. As used herein, the terms "binding to a substrate" and "immobilizing" are interchangeable as applied to DNA binding and immobilization.

The term "taggant" as used herein denotes a DNA or RNA marker, and optionally the DNA marker can be in combination with a second marker substance. The marker DNA and the additional one or more markers, when present, are affixed to an object to indicate a property of the object, such as for instance its source of manufacture.

The term "PCR" refers to a polymerase chain reaction. PCR is an amplification technology useful to expand the number of copies of a template nucleic acid sequence via a temperature cycling through melting, re-annealing and polymerization cycles with pairs of short primer oligonucleotides complementary to specific sequences bordering the template nucleic acid sequence in the presence of a DNA polymerase, such as a thermostable DNA polymerase such as the thermostable Taq polymerase originally isolated from the thermophillic bacterium (*Thermus aquaticus*). PCR includes, but is not limited, to standard PCR methods, where in DNA strands are copied to provide a million or more copies of the original DNA strands (e.g. PCR using random primers: See for instance PCR with Arbitrary Primers: Approach with Care. W. C. Black IV, Ins. Mol. Biol. 2: 1-6, December 2007); Real-time PCR technology, wherein the amount of PCR products can be monitored at each cycle (Real time quantitative PCR: C. A. Heid, J. Stevens, K. J. Livak and P. M. Williams, 1996 Genome Research 6: 986-994); Reverse transcription-PCR wherein RNA is first copied in DNA stands and thereafter the DNA strands are amplified by standard PCR reactions (See for example: Quantitative RT-PCR: Pitfalls and Potential: W. F. Freeman, S. J. Walker and K. E. Vrana; BioTechniques 26:112-125, January 1999).

The term "monomer" as used herein refers to any chemical entity that can be covalently linked to one or more other such entities to form an oligomer or a polymer. Examples of "monomers" include nucleotides, amino acids, saccharides, amino acids, and the like.

The term "nucleic acid" means a polymer composed of nucleotides which can be deoxyribonucleotides or ribonucleotides. These compounds can be natural or synthetically produced deoxyribonucleotides or ribonucleotides. The synthetically produced nucleic acid can be of a naturally occurring sequence, or a non-natural unique sequence.

The terms "ribonucleic acid" and "RNA" denote a polymer composed of ribonucleotides. The terms "deoxyribonucleic acid" and "DNA" denote a polymer composed of deoxyribonucleotides.

The term "nucleotide" means a monomeric unit comprising a sugar phosphate, usually ribose-5'-phosphate or 2'-deoxyribose-5'-phosphate covalently bonded to a nitrogen-containing base, usually, adenine (A), guanine (G), cytosine (C), or thymine (T) in the case of a deoxyribonucleotide, and usually, adenine (A), guanine (G), cytosine (C), or uracil (U) in the case of ribonucleotides.

The term "oligonucleotide" as used in this specification refers to single or double stranded polymer composed of covalently nucleotide monomers forming a chain of from two to about twenty nucleotides in length.

The term "polynucleotide" as used in this specification refers to single or double stranded polymer composed of covalently nucleotide monomers forming a chain of generally greater than about twenty nucleotides in length.

Nucleic acids having a naturally occurring sequence can hybridize with nucleic acids in a sequence specific manner That is they can participate in hybridization reactions in which the complementary base pairs A:T (adenine:thymine) and G:C (guanine:cytosine) form intermolecular (or intramolecular) hydrogen bonds and cooperative stacking interactions between the planar neighboring bases in each strand through Pi electrons, together known as Watson-Crick base pairing interactions. The bases of the nucleic acid strands can also hybridize to form non-Watson-Crick base pairs by so-called "wobble" interactions in which G (guanine) pairs with U (uracil), or alternatively, I (inosine) pairs with C (cytosine), U (uracil) or A (adenine), but with lower binding energies than the normal Watson-Crick base pairing interactions.

Exemplary embodiments provide methods for tagging an object and recovering a taggant from an object without disturbing the appearance of the object.

Exemplary embodiments of the present disclosure also provide methods for authenticating an object using taggants that have been incorporated onto an object or into a liquid for binding of an activated DNA taggant.

Taggants

Merchandise/products/objects can be embedded with designer DNA chains, such as custom gene vectors with specific genetic sequences that encode a protein or sequence with telomeres which will shorten each time the taggant is processed. These vectors can be removed from the objects and processed according to molecular biological techniques available to an art worker to produce the specific protein encoded by the vector. This protein can then be detected. These genetic sequences can be randomized and customized for each product SKU and further tailored to specific production dates. During authentication, the specific protein produced could be treated with a reagent that could be controlled by, for example a high-end brand, that could react with another protein in a detectable fashion, produce a specific odor, luminesce, fluoresce, or provide a temporary color. Further, those custom DNA taggants could be engineered to degrade over a specific amount of time. Even if one could sequence the vector, one would still have to know the specific reagent site, and the resulting detection/taggant molecule. Further, the cost to do such reverse engineering would be cost prohibitive given the temporal nature of those valid chains.

The taggants of the present disclosure include, for example, nucleic acid taggants. Nucleic acid is a general term for deoxyribonucleic acid (DNA) or ribonucleic acid (RNA), and can be synthetic, or derived from an animal, a plant, a bacterium, a virus, a fungus, or a synthetic vector or a fragment of any of the above-listed nucleic acids, etc. It should be noted that a synthetic nucleic acid can have a sequence of a naturally occurring nucleic acid of an animal, plant, bacterium, fungus, virus or any other organism or synthetic vector. Alternatively, a synthetic nucleic acid can have a unique sequence not found in nature. It should be understood that such unique non-natural sequences may have stretches of sequences which are found in nature, but the entire non-natural sequence is unique and is not found in any plant, animal or virus or any other natural organism. In particular, the nucleic acid sequence encoding the element of data or indicia encrypted or encoded in the taggant of the disclosure is a unique, non-natural sequence and thereby is adapted for use in authentication of an object of interest.

Thus, the taggants of the disclosure can be made recombinantly or synthetically. The DNA taggant can be natural DNA, whether isolated from natural sources or synthetic; or the DNA taggant can be a synthetically produced non-natural sequence. All or a portion of the DNA may comprise an identifiable sequence.

a) Telomeres—A telomere is a region of repetitive nucleotide sequences at each end of a chromosome, which protects the end of the chromosome from deterioration or from fusion with neighboring chromosomes. For vertebrates, the sequence of nucleotides in telomeres is TTAGGG, with the complementary DNA strand being AATCCC, with a single-stranded TTAGGG overhang. This sequence of TTAGGG is repeated approximately 2,500 times in humans. In humans, average telomere length declines from about 11 kilobases at birth to less than 4 kilobases in old age.

During chromosome replication, the enzymes that duplicate DNA cannot continue their duplication all the way to the end of a chromosome, so in each duplication the end of the chromosome is shortened (this is because the synthesis of Okazaki fragments requires RNA primers attaching ahead on the lagging strand). The telomeres are disposable buffers at the ends of chromosomes which are truncated during cell division; their presence protects the genes before them on the chromosome from being truncated instead. The telomeres themselves are protected by a complex of shelterin proteins, as well as by the RNA that telomeric DNA encodes (TERRA).

Over time, due to each cell division, the telomere ends become shorter.

In some embodiments, the DNA taggants include telomere sequences at their 5' and 3' ends. In humans, the amount of terminal (TTAGGG)n, telomeric DNA decreases during aging of various somatic cell types in vitro and in vivo. In some embodiments, the DNA taggant comprises double stranded DNA with a specific sequence with telomere sequences at each end of the specific sequence. The specific sequences can code for the authentication information described herein. DNA taggants useful in the disclosure can include any suitable length DNA taggant, such as for instance, in one example, the DNA taggant is a double stranded DNA oligomer having a length of between about 40 base pairs and about 1000 base pairs. In other embodiments the DNA taggant is a double stranded DNA oligomer with a length of between about 80 and 500 base pairs. In another embodiment the DNA taggant is a double stranded DNA oligomer having a length of between about 100 and about 250 base pairs. At the 5' and 3'ends of each of the base pairs is a telomeric sequence (TTAGGG)n (wherein is n is from 1 to about 50 or more, including 1, 2, 3, 4, 5, 6, 7, 8, 9, 10, 11, 12, 13, 14, 15, 16, 17, 18, 19, 20, 21 as so on).

When such a taggant is removed from an object, the size of the taggant is determined. The taggant is then placed in a somatic eurkaryotic cell, such as a fibroblast cell (by methods available to an art worker) and allowed to replicate. The replication will generate a shortened fragment due to telomere shortening. The shorter fragment is analyzed for length and sequence and then applied back on the object from which the original taggant was obtained.

This adds another layer of complexity and unique identifier to the object. This method can also be used to not only authenticate an object, but also to track, for example, how many times an object has been sold and/or limit the number of times an object can be sold (each time it is sold, the taggant is replicated, thus it is shortened due to the nature of the telomeres and the unique shorter DNA taggant is applied to the object from which the original taggant was obtained from). For example, if, upon transfer of an object, the buyer applies a DNA taggant authentication process (to verify it is an authentic object) which during authentication, the DNA strand is shortened/degraded. This constitutes the first transfer of title. Upon subsequent resale of the item, the same authentication process applied (to the now shorter strand applied to the item after the previous authentication), the DNA strand is shortened again. At a predetermined point, the strand is so shortened/degraded that further authentication can no longer occur.

In other embodiments there is provided intentional invalidation of the taggant. For example, this could be used when property is seized by authorities (to prevent theft and resale after being in police custody). It could also be used in a situation where an item is sold for an uncommonly large price as the prior owner is going to destroy the taggant, making the new owner the last and final owner. This could be done with oxidation or any number of available procedures. In one embodiment, the DNA taggant is removed, the telomeres are cleaved, such as through predetermined exonuclease sites, and then the DNA is reapplied, thereby leaving the rest of the encoded strand intact for validation of authenticity. In other words, while the absence of any remaining telomeres would end title transfer, you would still need the remaining chain to validate its authenticity.

DNA taggants recovered from the object can be amplified by polymerase chain reaction (PCR) and resolved by gel electrophoresis. Since the sequence of the nucleic acid taggants of the present disclosure are unique and specific to the tagged object, the original nucleic acid can be amplified only by use of primers having specific sequences complementary to a portion of the unique taggant sequence. Through this procedure, if the examined object carries the original nucleic acid, the PCR procedure will amplify extracted nucleic acid to produce amplicons of a predetermined size and a sequence identical to a portion of the original nucleic acid sequence of the taggant. In contrast, if the sample recovered from the examined object does not include the unique nucleic acid corresponding to the authentic object, there will likely be no amplified nucleic acid product, or if the primers do amplify the recovered nucleic acid to produce one or more random amplicons, these one or more amplicons cannot have the unique taggant nucleic acid sequence from the authentic object. Furthermore, the random amplicons derived from counterfeit articles are also of random lengths and the likelihood of producing amplicons of the exact lengths specified by the taggant-specific primers is vanishingly small. Therefore, by comparing the sizes of PCR products, the authenticity of labeled objects can be verified, non-authentic objects can be screened and rejected and anti-counterfeit screening purpose is then achieved.

b) Vector—Some embodiments of the disclosure provide expression vectors comprising specific nucleic acid sequences and/or coding for specific detectable marker proteins, including, but not limited to, green fluorescent protein (GFP), Luciferase—luciferin, β-glucuronidase—β-D-glucuronic acid (GUS assay), β-galactosidase—galactosides like X-gal (blue-white screen). An expression vector, otherwise known as an expression construct, is usually a plasmid or virus designed for gene expression in cells. The vector is used to introduce a specific gene into a target cell and can commandeer the cell's mechanism for protein synthesis to produce the protein encoded by the gene. Expression vectors are basic tools in biotechnology for the production of proteins.

The vector is engineered to contain regulatory sequences that act as enhancer and promoter regions and lead to efficient transcription of the gene carried on the expression vector. The goal of a well-designed expression vector is the efficient production of protein, and this may be achieved by the production of significant amount of stable messenger RNA, which can then be translated into protein. *Escherichia coli* is commonly used as the host for protein production, but other cell types may also be used.

An expression vector has a number of elements for gene expression. These can include a promoter, the correct translation initiation sequence such as a ribosomal binding site and start codon, a termination codon, and a transcription termination sequence. There are differences in the machinery for protein synthesis between prokaryotes and eukaryotes, therefore the expression vectors must have the elements for expression that is appropriate for the chosen host. For example, prokaryotes expression vectors would have a Shine-Dalgarno sequence at its translation initiation site for the binding of ribosomes, while eukaryotes expression vectors would contain the Kozak consensus sequence.

The promoter initiates the transcription and is therefore the point of control for the expression of the cloned gene. The promoters used in expression vector are normally inducible, meaning that protein synthesis is only initiated when required by the introduction of an inducer such as IPTG. Gene expression however may also be constitutive (i.e. protein is constantly expressed) in some expression vectors.

After the expression of the gene product, it may be necessary to purify the expressed protein. A purification tag may be added to the cloned gene. This tag could be histidine (His) tag or fusion partners such as glutathione S-transferase or maltose-binding protein. Some of these fusion partners may also help to increase the solubility of some expressed proteins.

In one embodiment, the telomere taggant and/or vector taggant are useful alone, in the combination together or in combination with any other suitable detectable or traceable marker, for example, a chemical marker or a biological marker. In an embodiment of the methods of the present disclosure, the marker is selected from a UV fluorophore, a ceramic IR marker, Up Converting Phosphor (UCP) infrared (IR) marker, UV marker, other DNA, an amino acid, a peptide, a protein, a lipid, a sugar, a polysaccharide, a pheromone, a scent, a trace element, a rare earth element, or a combination of any two or more thereof.

In an embodiment of the present disclosure, the taggant includes a nucleic acid. In one embodiment, the taggant consists essentially of DNA (e.g., telomere taggant and/or vector taggant) and no other significant component useful for identification or authentication.

Tagged Objects and Encoded Information

Any object that comprises a substantially solid surface may be marked with the nucleic acid taggant (tag). For example, a DNA tag and optional additional taggants according to exemplary embodiments of the present disclosure may be used to mark ownership of objects. Examples of such object may include, but are not limited to, ceramic surfaces, plastic films, vinyl sheets, magnetic strip cards, souvenirs, paper goods, money, bank notes, bonds, checks, security documents or any other printed matter, jewelry, including but not limited to, precious stones, rings, earrings, necklaces, watches and the like, works of art, including but not limited to, sculptures, paintings and the like; electronic goods, such as, but not limited to computers, computer peripheral devices, printers, microchips, disc drives, televisions, radios, DVD players, CD players, sound systems and the like; furniture, appliances, antiques, fiber or fabric, clothing or accessories, for example, but not limited to, purses (e.g., luxury handbags), shoes, belts, sunglasses, and other personal possessions, for example, but not limited to, cameras, automobiles, bicycles, motorcycles, luggage and the like, and sports collectibles and other collectibles (e.g., collectible sneakers) or any item of value.

It is also contemplated that the nucleic acid tags may be employed on or in personal identification documents, for example, but not limited to passports, driver's licenses, health cards, identification cards, Medicare cards, bank cards, credit cards, birth certificates and the like.

Nucleic acid taggants can also be added to a liquid composition. The liquid composition can be any be any suitable liquid composition, such as for instance, a printing ink, a dye or a spray. The liquid can also be a perfume or cologne.

The authenticity of these objects can then be verified by identifying the taggants bound or covalently bonded thereon through, for example, methods described in further detail below.

In one embodiment, the taggant is not endogenous to the object it is applied to/embedded in. In other words, the DNA sequence of the taggant is not present in the tagged object.

The taggant that has been applied onto an object provides a traceable nucleic acid taggant. The traceable nucleic acid taggant can be applied over all or part of the object to be identified, validated, authenticated, or if the object is an item of commerce, the item can be tracked at any point through the stream of commerce.

The taggant can be, for example, specific to the company or the type of item (e.g. a model number), specific to a particular lot or batch of the item (lot number), or specific to the actual item, as in, for instance, a serial number unique to the item. In addition, the taggant can indicate any one or more of a variety of other useful items of data; for example, the taggant can encode data that indicates the name and contact information of the company that manufactured the tagged product or item, the date of manufacture, the distributor and/or the intended retailer of the product or item. The taggant can also indicate, for example and without limitation, component data, such as the source of the component incorporated into the item or the identity of the production plant or machinery that was used in the manufacture of the product or item; the date that the product or item was placed into the stream of commerce, the date of acceptance by the distributor and/or the date of delivery to the retailer, date of sale to a purchaser, and any other useful commercial, or other data such as for instance personal information of the owner. Each element of data or indicia can be encrypted or encoded in the taggant and can be deciphered from taggant recovered from the object and decoded or decrypted according to the methods described herein. The decoded or decrypted data can then be used to verify the properties of the object, or to authenticate the object, or to exclude counterfeit items.

The nucleic acid tag can exhibit the following properties: DNA is stable/protected from degradation after the composition is applied to an object, asset, article or the like. For example, the DNA is protected from being degraded for a period of at least about 6 months, including about 1 year, such as about 2 years, or about 5 years, or about 10 years, even about 20 years, or longer. By the term "degraded" or "degradation" it is meant that the DNA comprises less than 50% cleavage of the DNA, including less than about 30% cleavage, such as less than about 20% cleavage, including less than about 10% cleavage, and less than about 1% cleavage of the original DNA contained in the composition. By the term "cleavage" it is meant either exonuclease cleavage, endonuclease cleavage or a combination thereof.

Methods of Binding Taggant to Substrate/Object

The nucleic acid taggant can be brushed, sprayed or soaked on, with or without an incorporated polymer or a polymer coating (see US published pat appln 20090253127; incorporated herein in its entirety by reference). Any method may be used as long as the object and DNA taggant is not damaged.

In some embodiments, the DNA tag is exposed to alkaline conditions prior to contacting the taggant to the substrate/object. Alkali metals are members of Group I in the periodic table consisting of the elements lithium (Li), sodium (Na), potassium (K), rubidium (Rb), cesium (Cs) and francium (Fr). These alkali metals of the periodic table are elements that exhibit homologous chemical characteristics.

In one embodiment, the DNA taggant is exposed to alkaline conditions followed by contacting the deoxyribonucleic acid to the substrate. The DNA bound to the substrate is available for binding by hybridization probes, PCR amplification and DNA sequencing methods.

In one embodiment, the alkaline conditions are produced by mixing the deoxyribonucleic acid with an alkaline solution having a high pH, for instance the pH of the alkaline solution can be a pH of about 9.0 or higher; a pH of about 10.0 or higher; a pH of about 11.0 or higher, or even a pH of about 12.0 or higher, and contacting the deoxyribonucleic acid that has been exposed to the alkaline conditions with the substrate. In one embodiment, the alkaline solution is a solution of a hydroxide of an alkali metal.

Another embodiment of the present disclosure provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of a hydroxide of an alkali metal and the alkali metal is selected from the group consisting of lithium (Li), sodium (Na), rubidium (Rb), and cesium (Cs).

Another embodiment of the present disclosure provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of an alkali metal hydroxide, wherein the alkali metal hydroxide is selected from the group consisting of lithium hydroxide (LiOH), sodium hydroxide (NaOH) and cesium hydroxide (CsOH). In one embodiment, the alkali metal hydroxide is sodium hydroxide (NaOH).

These and other alkali binding methods/compositions are incorporated by reference from U.S. Pat. No. 9,790,538.

Removal and/or Analysis of Taggant on an Object

DNA may be recovered from an object tagged with the taggants provided herein by a variety of methods as would be known in the art. For example, but not wishing to be limiting in any manner, the object may be wiped with a solvent, solution or combination thereof which is removing the nucleic acid taggant (e.g., DNA) and dissolving any polymer associated therewith thereby providing access to the taggant (e.g., DNA) contained therein.

It is also contemplated that a taggant may be removed from an object, for example, but not limited to gentle abrasion or mild scraping with an appropriate implement. Such implements may include but are not limited to a file, sand paper and the like. In some instances, a taggant may be applied to a portion of the object which is designed for removal, such as cutting or breaking/tearing a piece of the object away (e.g., an additional flap of fabric or piece of a belt).

The DNA recovered from an object may be extracted, washed, purified, concentrated, amplified or a combination thereof using well-known methods in the art. For example, the DNA may be subjected to one or more precipitations, extractions, centrifugations, filtrations, microfiltrations, chromatography separations, electrophoresis separations or a combination thereof. In addition, the DNA that is isolated may be subjected to one or more enzymatic reactions including, but not limited to any cloning step that would be known in the art, amplification steps such as but not limited to polymerase chain reaction (PCR) or the like.

In an embodiment of the present disclosure, which is not meant to limit the disclosure in any way, add in telomerase and protein making the DNA isolated from an object treated is purified and amplified by PCR or a similar procedure as would be known in the art. Once amplified, the DNA may be sequenced, subjected to restriction length fragment polymorphism, microsatellite, short tandem repeat (STR) analysis or the like as a means to provide information on the owner of the object. The information may be used to search a database or data-structure to identify the object and/or its details.

Database

The method of the present disclosure may also comprise a step of recording or registering objects that have been tagged into a database, data structure or the like which may be, but is not limited to being an electronic database. The electronic database may be online or off-line. In an embodiment, the electronic database is online and information may be transmitted to the database via the internet. Without wishing to be limiting in any manner, in such an embodiment, a subject may be able to list and optionally describe objects that have been tagged. Information that may be recorded or registered can include, but is not limited to owner or manufacturer's name, address, telephone number, fax number, email address, description of object tagged, location that objects have been tagged, date object was purchased or acquired, place object was purchased or acquired, serial numbers or other identification numbers, etc.

The methods described herein may optionally comprise the step of searching a database, or data-structure to confirm or deny the objects authenticity. For example, one embodiment of the present disclosure provides a method for authenticating an object which includes providing an object to which a taggant is bound or covalently bonded, sampling the object for identification, tracking, or verifying the authenticity of the object by identifying the unique traceable deoxyribonucleic acid (DNA) taggant. In one embodiment, the unique taggant is a DNA taggant which may or may not have a unique DNA sequence, but has a unique length based on the telomerase and the number of times the taggant has been replicated. The unique DNA sequence and/or length is stored in a database that matches the unique DNA sequence and/or length to the data elements corresponding to the object which is bound to or covalently bonded to the unique taggant. The database can in turn be located on a computer that can be accessed in order to locate, track, authenticate and verify the identity of the tagged object from which the taggant was detected.

Kits

The present disclosure also provides a kit for marking objects with a nucleic acid taggant. The kit may comprise DNA taggant, a taggant applicator, for example a brush or the like, instructions for marking objects with the taggant, one or more forms that may be used to list items marked with the taggant of the present disclosure, a logon ID and password or unique identifier code or number for a system, database or data structure that allows a subject to record items that have been marked with the taggant into the database, or a combination thereof.

In an embodiment of the present disclosure, which is not meant to be considered limiting in any manner, the unique registration code/number may provide the owner with private access to a secure web-based application, wherein individuals record or register information concerning their physical objects and assets treated with the taggant thereby linking an owner to its asset or physical property. The secure web-based application may record information about the individual, for example, but not limited to the name or codename of the individual and the address as well as the answer to one or more generic questions about the individual.

The taggants may be provided in one or more containers, for example, but not limited to one or more vials, screw cap tubes, Eppendorf tubes, or the like. It is also contemplated that the taggants may be provided as a single use container that may be employed to mark one or more objects.

Certain embodiments are described herein. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the disclosure unless otherwise indicated herein or otherwise clearly contradicted by context.

References have been made to publications, patents and/or patent applications (collectively "references") throughout this specification. Each of the cited references is individually incorporated herein by reference for their particular cited teachings as well as for all that they disclose.

The invention claimed is:

1. A method of processing an object including a nucleic acid taggant for authenticating or tracking the object, the method comprising:
   obtaining the object including the nucleic acid taggant, the nucleic acid taggant including telomeres;
   treating the object to remove the nucleic acid taggant;
   cleaving the telomeres of the nucleic acid taggant; and
   reapplying the nucleic acid taggant without the telomeres to the object as an indication of authenticity.

2. The method of claim 1, wherein the cleaving of the telomeres of the nucleic acid taggant is through predetermined exonuclease sites.

3. The method of claim 2, wherein the nucleic acid taggant without the telomeres is additionally an indication of an end of title transfer.

4. The method of claim 2, wherein the nucleic acid taggant is a DNA taggant.

5. The method of claim 2, wherein the object consists of at least one of money, a bank note, a bond, a check, a security document, a ring, an earring, a necklace, a watch, a sculpture, a painting, a computer, a computer peripheral device, a printer, a microchip, a disc drive, a television, a radio, a DVD player, a CD player, a sound system, furniture, an appliance, an antique, clothing, a handbag, a shoe, a belt, sunglasses, a camera, an automobile, a bicycle, a motorcycle, luggage, a sports collectible, ceramic, plastic, vinyl, paper, stone, metal, or liquid.

6. A method of processing an object including a nucleic acid taggant for tracking the object, the method comprising:
   obtaining the object including the nucleic acid taggant, the nucleic acid taggant including telomeres;
   treating the object to remove the nucleic acid taggant;
   cleaving the telomeres of the nucleic acid taggant; and
   reapplying the nucleic acid taggant without the telomeres to the object as an indication of title transfer.

7. The method of claim 6, wherein the object consists of at least one of money, bank notes, bonds, checks, or security documents.

8. The method of claim 6, wherein the object consists of at least one of stones, rings, earrings, necklaces, or watches.

9. The method of claim 6, wherein the object consists of at least one of sculptures or paintings.

10. The method of claim 6, wherein the object consists of at least one of computers, computer peripheral devices, printers, microchips, disc drives, televisions, radios, DVD players, CD players, or sound systems.

11. The method of claim 6, wherein the object consists of at least one of furniture, appliances, antiques, clothing, handbags, shoes, belts, or sunglasses.

12. The method of claim 6, wherein the object consists of at least one of cameras, automobiles, bicycles, motorcycles, luggage, or sports collectibles.

13. The method of claim 6, wherein the object consists of at least one of ceramic, plastic, vinyl, paper, stone, metal, or liquid.

14. The method of claim 6, wherein the nucleic acid taggant is a DNA taggant.

15. A method of processing an object including a nucleic acid taggant for tracking the object, the method comprising:
    obtaining the object including the nucleic acid taggant, the nucleic acid taggant including telomeres;
    treating the object to remove the nucleic acid taggant;
    cleaving the telomeres of the nucleic acid taggant; and
    reapplying the nucleic acid taggant without the telomeres to the object as an indication of a number of times the object has been transferred.

16. The method of claim 15, wherein the cleaving of the telomeres of the nucleic acid taggant is through predetermined exonuclease sites.

17. The method of claim 15, wherein the nucleic acid taggant without the telomeres is additionally an indication of authenticity.

18. The method of claim 15, wherein the nucleic acid taggant is a DNA taggant.

19. The method of claim 15, wherein the object consists of at least one of money, a bank note, a bond, a check, a security document, a ring, an earring, a necklace, a watch, a sculpture, a painting, a computer, a computer peripheral device, a printer, a microchip, a disc drive, a television, a radio, a DVD player, a CD player, a sound system, furniture, an appliance, an antique, clothing, a handbag, a shoe, a belt, sunglasses, a camera, an automobile, a bicycle, a motorcycle, luggage, a sports collectible, ceramic, plastic, vinyl, paper, stone, metal, or liquid.

20. The method of claim 15, wherein the nucleic acid taggant without the telomeres is additionally an indication of an end of title transfer.

* * * * *